United States Patent

Turner et al.

[11] Patent Number: 6,140,271
[45] Date of Patent: Oct. 31, 2000

[54] 1-ALKYL-4-BENZOYL-5-HYDROXYPYRAZOLE COMPOUNDS AND THEIR USE AS HERBICIDES

[75] Inventors: James A. Turner, Indianapolis; Monte R. Weimer, Pittsboro; Johnny L. Jackson, Indianapolis, all of Ind.

[73] Assignee: Dow AgroSciences LLC, Indianapolis, Ind.

[21] Appl. No.: 09/316,903

[22] Filed: May 22, 1999

Related U.S. Application Data

[60] Provisional application No. 60/086,576, May 22, 1998.

[51] Int. Cl.[7] .................. A01N 43/56; C07D 231/10; C07D 305/06
[52] U.S. Cl. .................. 504/282; 548/369.4; 549/511
[58] Field of Search .................. 548/369.4; 549/511; 504/282

[56] References Cited

U.S. PATENT DOCUMENTS

| | | |
|---|---|---|
| Re. 34,408 | 10/1993 | Tanaka et al. . |
| Re. 34,779 | 11/1994 | Oya et al. . |
| 4,063,925 | 12/1977 | Konotsune et al. . |
| 4,146,540 | 3/1979 | Avar et al. . |
| 4,230,481 | 10/1980 | Nishiyama et al. . |
| 4,643,757 | 2/1987 | Baba et al. . |
| 4,744,815 | 5/1988 | Baba et al. . |
| 4,885,022 | 12/1989 | Baba et al. . |
| 4,948,887 | 8/1990 | Baba et al. . |
| 4,986,845 | 1/1991 | Oya et al. .................. 71/92 |

FOREIGN PATENT DOCUMENTS

| | | |
|---|---|---|
| 0 530 642 A1 | 3/1993 | European Pat. Off. . |
| WO 93/17016 | 9/1993 | WIPO . |
| WO 96/26206 | 8/1996 | WIPO . |
| WO 97/41106 | 11/1997 | WIPO . |
| WO 98/42677 | 10/1998 | WIPO . |
| WO 98/50379 | 11/1998 | WIPO . |

*Primary Examiner*—Joseph K. McKane
*Assistant Examiner*—Sonya Wright
*Attorney, Agent, or Firm*—Craig E. Mixan

[57] ABSTRACT

1-Alkyl-4-benzoyl-5-hydroxy-1H-pyrazole compounds in which the benzoyl moiety is substituted in the 2-position with groups such as halo or alkyl, in the 4-position with an alkylsulfonyl group, and in the 3-position with a 3-oxetanyloxy or an oxetanylmethoxy substituent were prepared and found to be useful for the control of a variety of broadleaf and grassy weeds. The compounds have favorable environmental and toxicological properties and can be used to control undesirable vegetation in crops.

32 Claims, No Drawings

1-ALKYL-4-BENZOYL-5-HYDROXYPYRAZOLE COMPOUNDS AND THEIR USE AS HERBICIDES

CROSS-REFERENCE TO RELATED APPLICATIONS

This application claims the benefit of U.S. Provisional Application No. 60/086,576, filed May 22, 1998.

BACKGROUND OF THE INVENTION

This invention relates to novel 1-alkyl-4-benzoyl-5-hydroxypyrazole compounds and to the use of these compounds as herbicides.

A number of 1-alkyl-4-benzoyl-5-hydroxypyrazole compounds and their herbicidal utility have been disclosed in the art, for example, in U.S. Pat. Nos. 4,230,481, 4,063,925, 4,643,757, 4,744,815, 4,885,022, 4,948,887, RE34,779, RE34,408, and RE34,423. Compounds of this type having specified alkoxy substituents, including some aliphatic heterocyclyloxy substituents, at the 3-position of the benzoyl ring were disclosed U.S. Pat. No. 4,986,845 (RE-34,779).

None of the presently known 1-alkyl-4-benzoyl-5-hydroxypyrazole compounds, however, possess sufficient herbicidal activity coupled with sufficient crop selectivity and desirable toxicological and environmental properties to achieve broad commercial acceptance. It would be highly desirable to discover related compounds that are more potent, more selective, or broader spectrum in their herbicidal activity and/or that have improved toxicological or environmental properties.

SUMMARY OF THE INVENTION

It has now been found that 1-alkyl-4-benzoyl-5-hydroxypyrazole compounds possessing a 4-membered aliphatic oxacyclyloxy or 4-membered aliphatic oxacyclylmethoxy substituent in the 3-position and selected substituents in the 2- and 4-positions of the benzoyl moiety are potent herbicides with a broad spectrum of weed control and excellent crop selectivity. The compounds, further, possess excellent toxicological and environmental profiles.

The invention includes benzoylpyrazole compounds of Formula I:

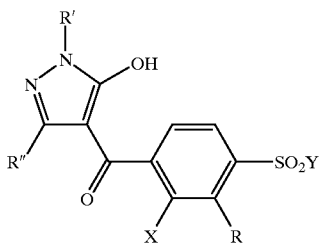

wherein
X represents F, Cl, Br, $CH_3$ or $OCH_3$;
Y represents $CH_3$, $C_2H_5$, or $CH(CH_3)_2$;
R represents 3-oxetanyloxy, 3-oxetanylmethoxy, or 2-oxetanylmethoxy, each optionally substituted with methyl;
R' represents $C_1$–$C_4$ alkyl, $C_3$–$C_4$ alkenyl, or $C_3$–$C_4$ alkynyl;
R" represents H or $CH_3$; and the agriculturally acceptable salts and esters thereof.

Compounds of Formula I wherein X represents chloro or methyl, wherein Y represents methyl, wherein R represents 3-oxetanyloxy, wherein R' represents methyl or ethyl, and wherein R" represents hydrogen are often independently preferred.

The invention includes herbicidal compositions containing the benzoylpyrazole compounds of Formula I in combination with an agriculturally acceptable adjuvant or carrier as well as a method of use of the compounds to kill or control undesirable vegetation by application of an herbicidal amount of the compound to the vegetation or to the locus of the vegetation. The use of the compounds to kill or control grass and broadleaf weeds in corn, wheat, barley, and rice is a preferred utility and postemergence application of the compounds to the undesirable vegetation is a preferred method of application.

The invention further includes benzoic acid intermediates useful in preparing the herbicidal benzoylpyrazole compounds of Formula I.

DETAILED DESCRIPTION OF THE INVENTION

The herbicidal compounds of the present invention are benzoylpyrazole compounds of Formula I:

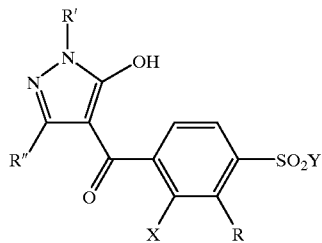

These compounds are characterized by possessing a pyrazole heterocycle moiety substituted in the 1-position with an alkyl group, in the 5-position with an hydroxy group, and in the 4-position with a benzoyl moiety. Substitution in the 3-position is optional. The benzoyl moiety is characterized by being substituted in the 3-position with an optionally methylated 4-membered aliphatic oxacyclyloxy or 4-membered aliphatic oxacyclylmethoxy substituent, in the 4-position with a lower alkylsulfonyl substituent, and in the 2-position with a halo, methyl, or methoxy substituent. The compounds include the salt and ester compounds obtained by derivatization of the 5-position hydroxy group of the pyrazole moiety.

Compounds of Formula I are sometimes named as (2,3,4-trisubstituted phenyl)(1-alkyl-5-hydroxy-1H-pyrazol-4-yl)methanone compounds, but are more often referred to in the art as 1-alkyl-4-(2,3,4-trisubstituted benzoyl)-5-hydroxy-1H-pyrazole compounds. The latter terminology is used herein. The compounds of Formula I are, further, sometimes referred to as 1-alkyl-4-(2,3,4-trisubstituted benzoyl)-1H-pyrazolin-5-one compounds; that is, as the keto tautomers of the formula illustrated.

The invention includes compounds of Formula I wherein the pyrazole moiety is substituted in the 1-position (R') with an aliphatic hydrocarbyl group of 1 to 4 carbon atoms including compounds wherein R' represents a $C_1$–$C_4$ alkyl, $C_3$–$C_4$ alkenyl, or $C_3$–$C_4$ alkynyl group. Compounds wherein R' represents methyl, ethyl, 1-methylethyl, 1,1-dimethylethyl, and cyclo-propyl are typically preferred. Those wherein R' represents methyl or ethyl are typically more preferred.

Compounds of Formula I that are unsubstituted in the 3-position of the pyrazole moiety (R" represents hydrogen) or are substituted at that position with methyl are included in the invention. Generally, compounds wherein R" represents hydrogen are preferred. Compounds wherein R' represents methyl, ethyl, 1-methylethyl, 1,1-dimethylethyl, or cyclo-propyl and R" represents hydrogen are often preferred and those wherein R' represents methyl or ethyl and R" represents hydrogen are often of special interest.

The invention includes compounds of Formula I wherein the benzoyl moiety is substituted in the 4-position ($SO_2Y$) with a methylsulfonyl, ethylsulfonyl, or 1-methylethylsulfonyl group. Methylsulfonyl groups (Y represents methyl) are typically preferred.

Compounds of Formula I substituted in the 2-position of the benzoyl moiety (X) with a fluoro, chloro, bromo, methoxy, or methyl group are included in the invention. Compounds wherein X represents chloro are sometimes preferred and compounds wherein X represents methyl are sometimes preferred. Compounds wherein X represents chloro or methyl and Y represents methyl are often of special interest.

The most distinguishing characteristic of the compounds of the present invention is the 4-membered oxygen containing heterocylic moiety in the 3-position of the benzoyl moiety. These moieties can be further described as 4-membered aliphatic oxacyclyloxy or 4-membered aliphatic oxacyclylmethoxy moieties each optionally substituted with methyl. Suitable such moieties include 3-oxacyclobutanyloxy (3-oxetanyloxy), 3-oxacyclobutanylmethoxy (3-oxetanylmethoxy), and 3-oxacyclobutanylmethoxy (3-oxetanylmethoxy), which moieties are illustrated sequentially below:

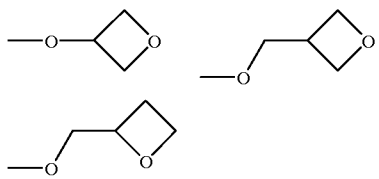

and methylated analogs. 1-Methyl-3-oxacyclobutanyloxy (3-methyl-3-oxetanyloxy) is an example of a methylated analog. 3-Oxetanyloxy is usually a preferred R group.

Compounds of Formula I wherein X represents chloro or methyl, Y represents methyl, and R represents 3-oxetanyloxy are often of special interest.

Compounds of Formula I wherein R' represents methyl or ethyl; R" represents hydrogen; X represents chloro or methyl; Y represents methyl, and R represents 3-oxacyclobutanyloxy (3-oxetanyloxy) are often preferred.

Specifically preferred compounds include 1-ethyl-4-(2-methyl-3-(3-oxetanyloxy)-4-methylsulfonylbenzoyl)-5-hydroxypyrazole and 1-ethyl-4-(2-chloro-3-(3-oxetanyloxy)-4-methylsulfonylbenzoyl)-5-hydroxypyrazole.

The compounds of Formula I are believed to be the compounds that actually kill or control undesirable vegetation and are typically preferred. Analogs of these compounds in which the hydroxy group of the pyrazole ring is derivatized to form a related substituent that can be transformed within plants or the environment to a hydroxy group possess essentially the same herbicidal effect and are within the scope of the invention. The agriculturally acceptable salts obtainable by treating an hydroxy compound of Formula I with, for example, a metal hydroxide, a metal carbonate, an amine or an aminium hydroxide compound and agriculturally acceptable esters obtainable, for example, by treating an hydroxy compound of Formula I with an acid chloride, such as an alkanoyl chloride, a benzoyl chloride, or an alkylsulfonyl chloride, are convertible to the hydroxy compound and are examples of the derivatives included in the invention. The 5-position hydroxy group of the pyrazole ring of the compounds of Formula I is weakly acidic and forms both salts and esters readily.

Agriculturally acceptable salts and esters are defined as those salts and esters of the 5-position hydroxy group of the pyrazole ring of the compounds of Formula I in which the cation or acid moiety is not, itself, significantly herbicidal to any crop being treated and is not significantly deleterious to the applicator, the environment, or the ultimate user of any crop being treated.

Suitable esters include those derived from optionally substituted aliphatic and aromatic carboxylic acids, examples of which are $C_1$–$C_8$ alkylcarboxylic acids, $C_3$–$C_8$ alkenylcarboxylic acids, and benzoic acid. Suitable esters further include alkylsulfonyl esters derived from alkylsulfonic acids. $C_1$–$C_4$ alkanoyl and benzoyl esters are generally preferred.

Suitable cations include, for example, those derived from alkali or alkaline earth metals and those derived from ammonia and amines. Preferred cations include sodium, potassium, magnesium, and aminium cations of the formula:

wherein $R^5$, $R^6$, and $R^7$ each, independently represents hydrogen or $C_1$–$C_{12}$ alkyl, $C_3$–$C_{12}$ cycloalkyl, or $C_3$–$C_{12}$ alkenyl, each of which is optionally substituted by one or more hydroxy, $C_1$–$C_8$ alkoxy, $C_1$–$C_8$ alkylthio or phenyl groups, provided that $R^5$, $R^6$, and $R^7$ are sterically compatible. Additionally, any two of $R^5$, $R^6$, and $R^7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethylamine, 2-methylthiopropylamine, bisallylamine, 2-butoxyethylamine, morpholine, cyclododecylamine, or benzylamine. Amine salts are often preferred forms of the compounds of Formula I because they are water soluble and lend themselves to the preparation of desirable aqueous based herbicidal compositions.

The terms alkyl, alkenyl, and alkynyl as used herein includes straight chain, branched chain, and cyclic moieties. Thus, typical alkyl groups are methyl, ethyl, 1-methylethyl, propyl, cyclopropyl, cyclopropylmethyl, methylcyclopropyl, and the like. Methyl, ethyl, and 1-methylethyl are often preferred.

Compounds of Formula I can generally be prepared by the reaction of an appropriate (3-halo-benzoyl)pyrazole compound of Formula II:

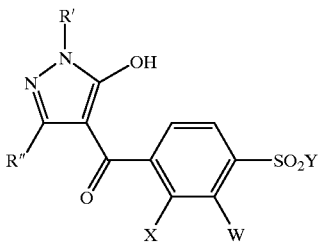

wherein W represents fluoro or chloro and R', R", X, and Y are as defined for compounds of Formula I with an alkali metal salt of 3-oxetanol (3-oxacyclobutan-1-ol), 3-oxetanylmethanol (3-oxacyclobutan-1-ylmethanol), or 2-oxetanylmethanol (2-oxacyclobutan-1-ylmethanol), which are illustrated sequentially in Formula III:

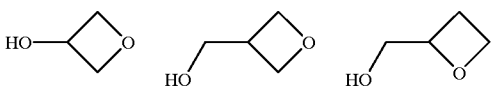

or a methylated analog. Compounds of Formula II wherein W represents fluoro are usually superior intermediates because they are more reactive than the corresponding chloro compounds and give better yields under milder conditions. The reaction is often carried out in a dipolar, aprotic solvent, such as N,N-dimethylformamide or N-methyl-2-pyrrolidinone, or in an excess of the alcohol of Formula III. The reactants and desired product of Formula I are generally soluble in such media, particularly at higher temperatures, which promotes the reaction. The reaction is generally carried out at temperatures of about 0° C. to about 100° C., preferably at about 20° C. to about 80° C. It is often convenient to carry out the reaction at ambient temperatures. The alkali metal salts of the compounds of Formula III can be pre-prepared or prepared in situ; they can be prepared by any of the methods known to those in the art. The compounds of Formula I obtained in the process can be recovered by conventional means. Typically, the reaction mixture is acidified with an aqueous acid, such as hydrochloric acid, and extracted with an organic solvent, such as ethyl acetate or dichloromethane. The organic solvent and other volatile components can be removed by distillation or evaporation to obtain the desired compound of Formula I. The compounds of Formula I prepared in this way can be purified by standard procedures, such as by recrystallization or chromatography.

The (3-fluoro- and 3-chlorobenzoyl)pyrazole compounds of Formula II can be prepared from 2-substituted-3-halo-4-alkylsulfonylbenzoic acids of Formula IV:

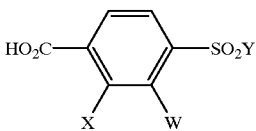

wherein W represents chloro or fluoro and X and Y are as defined for compounds of Formula I by reaction with a 1-alkyl-5-hydroxypyrazole compound of Formula V:

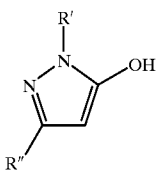

wherein R' and R" are as defined for compounds of Formula I. Suitable preparative methods are disclosed, for example, in U.S. Pat. Nos. 4,063,925, 4,885,022, and 4,986,845. One of these methods involves conversion of the benzoic acid compound of Formula IV to its acid chloride with thionyl chloride, coupling this acid chloride with a 5-hydroxypyrazole compound of Formula V in the presence of triethylamine, and rearranging the originally formed ester and/or amide product with a cyanide ion catalyst, typically supplied by adding acetone cyanohydrin or potassium cyanide. Another method involves the reaction of a benzoic acid compound of Formula IV with a 5-hydroxypyrazole compound of Formula V in the presence of dicyclohexylcarbodiimide and isomerization of the originally formed ester with a cyanide ion catalyst. The compounds of Formula II obtained by these methods can be recovered using the methods known in the art for related compounds.

2-Substituted-3-halo-4-alkylsulfonylbenzoic acid compounds of Formula IV can generally be prepared from 1-bromo-2-substituted-3-halo-4-alkylthiobenzene compounds by sequential treatment with butyl lithium and carbon dioxide in tetrahydrofuran followed by oxidation with hydrogen peroxide in acetic acid. Alternatively, these compounds can be prepared by oxidation of the same starting material with hydrogen peroxide in acetic acid followed by carbonylation with carbon monoxide in the presence of a palladium acetate:(diphenylphosphono)butane complex, sodium acetate, and ethanol. 1-Bromo-2-substituted-3-halo-4-alkylthiobenzene compounds can be prepared from 1-substituted-2-halo-3-alkylthiobenzene compounds by bromination in the presence of ferric chloride. Many 1-substituted-2-halo-3-alkylthiobenzene compounds can be prepared by treatment of 1-substituted-2-halobenzene compounds sequentially with butyl lithium and a dialkyl disulfide compound in tetrahydrofuran. Some 2-substituted-3-chloro-4-alkylsulfonylbenzoic acid compounds of Formula IV and their preparation are known in the art.

The compounds of Formula I can also generally be prepared from an appropriately substituted 3-alkoxybenzoic acid compound of Formula VI:

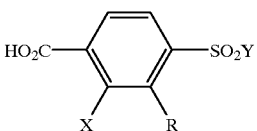

wherein X, Y, and R are as defined for compounds of Formula I and an appropriate 1-alkyl-5-hydroxypyrazole compound of Formula V:

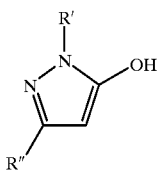

wherein R' and R" are as defined for compounds of Formula I. The coupling can be carried out under reaction conditions known in the art for reactions of other benzoic acid compounds with 1-alkyl-5-hydroxypyrazole compounds to form benzoylpyrazoles. Suitable preparative methods are disclosed, for example, in U.S. Pat. Nos. 4,063,925, 4,885,022, and 4,986,845 and are described hereinabove for the reaction of compounds of Formula IV with those of Formula V. The compounds of Formula I obtained by these methods can be recovered using the methods known in the art for related compounds.

The 3-alkoxybenzoic acid compounds of Formula VI can be prepared by the reaction of an appropriate 2-substituted-3-halo-4-alkylsulfonylbenzoic acid compound of Formula IV:

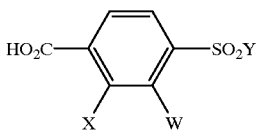

wherein W represents chloro or fluoro and X and Y are as defined for compounds of Formula I with alkali metal salt of 3-oxetanol, 3-oxetanylmethanol, or 2-oxetanylmethanol of Formula III or a methylated analog. Compounds of Formula IV wherein W represents fluoro are usually superior intermediates because they are more reactive than the corresponding chloro compounds and give better yields under milder conditions. The reaction is often carried out in a dipolar, aprotic solvent, such as N,N-dimethylformamide or N-methyl-2-pyrrolidinone, or in an excess of the alcohol of Formula III. The reactants and desired product of Formula VI are generally soluble in such media, particularly at higher temperatures, which promotes the reaction. The reaction is generally carried out at temperatures of about 0° C. to about 1000° C., preferably at about 20° C. to about 80° C. It is often convenient to carry out the reaction at ambient temperatures. The alkali metal salts of the compounds of Formula III can be pre-prepared or prepared in situ; they can be prepared by any of the methods known to those in the art. The compounds of Formula VI obtained in the process can be recovered by conventional means. Typically, the reaction mixture is acidified with an aqueous acid, such as hydrochloric acid, and extracted with an organic solvent, such as ethyl acetate or dichloromethane. The organic solvent and other volatiles can be removed by distillation or evaporation to obtain the desired compound of Formula VI. The compounds of Formula VI prepared in this way can be purified by standard procedures, such as by recrystallization or chromatography.

The alcohol compounds of Formula III and their preparation are known in the art. Most of the benzoic acid compounds of Formula IV and the 3-halobenzoyl)-pyrazole compounds of Formula II and methods for their preparation are known in the art. Other such compounds and methods for their preparation are disclosed herein in the Examples.

The compounds of Formula I have been found to be useful preemergence and postemergence herbicides. They can be employed at non-selective (higher) rates of application to control a broad spectrum of the vegetation in an area or at selective (lower) rates of application for the selective control of undesirable vegetation in grass crops, such as corn, wheat, barley, and rice, as well as in broadleaf crops, such as soybeans and cotton. It is usually preferred to employ the compounds post-emergence. It is further usually preferred to use the compounds to control a broad spectrum of weeds, including grassy weeds, such as barnyardgrass and giant foxtail, in corn, wheat, or barley crops. Use of the compounds to control undesirable vegetation in corn is especially indicated. While each of the benzoylpyrazole compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient which kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I post-emergence to relatively immature undesirable vegetation to achieve the maximum control of weeds.

Application rates of about 1 to about 500 g/Ha are generally employed in postemergence operations; for preemergence applications, rates of about 10 to about 1000 g/Ha are generally employed. The higher rates designated generally give non-selective control of a broad variety of undesirable vegetation. The lower rates typically give selective control and can be employed in the locus of crops.

The herbicidal compounds of the present invention are often best applied in conjunction with one or more other herbicides to obtain control of a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed in conjunction with the compounds of the present invention include sulfonamides such as metosulam, flumetsulam, cloransulam-methyl, diclosulam, and N-2,6-dichlorophenyl-5-ethoxy-7-fluoro[1,2,4]triazolo-[1,5-c]pyrimidine-2-sulfonamide, sulfonylureas such as chlorimuron, nicosulfuron and metsulfuron, imidazolidones such as imazaquin, imazethapyr and imazamox, phenoxyalkanoic acids such as 2,4-D and MCAA, pyridinyloxyacetic acids such as triclopyr and fluroxypyr, carboxylic acids such as clopyralid and dicamba, dinitroanilines such as trifluralin and pendimethalin, chloroacetanilides such as alachlor, acetochlor and metolachlor and other common herbicides including acifluorfen, bentazon, clomazone, fumiclorac, fluometuron, fomesafen, lactofen, linuron, isoproturon, and metribuzin. They can, further, be used in conjunction with glyphosate and glufosinate on glyphosate-tolerant or glufosinate-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and complementary other herbicides at the same time, either as a combination formulation or as a tank mix.

The compounds of the present invention can generally be employed in combination with known herbicide safeners, such as cloquintocet, furilazole, dichlormid, benoxacor, mefenpyr-ethyl, fenclorazole-ethyl, flurazole, and fluxofenim, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are hydroxyphenylpyruvate dioxygenase inhibitors in sensitive plants can be treated. Many glyphosate and glufosinate tolerant crops can be treated as well, alone or in combination with these herbicides.

While it is possible to utilize the benzoylpyrazole compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

EXAMPLES

The following Examples are presented to illustrate the various aspects of this invention and should not be construed as limitations to the claims.

1. Preparation of 3-Chloro-2-fluorothioanisole

A solution of 10 g (grams) (76 mmol (millimoles)) of 1-chloro-2-fluorobenzene in 75 mL (milliliters) of dry tetrahydrofuran (THF) was cooled with a dry ice/acetone bath and 34 mL (84 mmol) of 2.5M butyllithium was added dropwise under a nitrogen blanket over 45 min with stirring and cooling. The resulting solution was stirred for 2 hours at $-78°$ C. A solution of 8.1 mL (91 mmol) of dimethyl disulfide in 10 mL of dry THF was added with stirring over a 30-min period keeping the temperature below $-65°$ C. The mixture was allowed to warm to ambient temperature for 1 hour. It was then diluted with 75 mL of water. The resulting mixture was extracted with diethyl ether and the ether extract was dried over sodium sulfate and concentrated by evaporation under reduced pressure to obtain a yellow oil. This oil was purified by flash chromatography on 230–400 mesh silica gel eluting with a hexane/ethyl acetate mixture to obtain 9.0 g (69 percent of theory) of the title compound as a light yellow oil.

Elemental Analysis $C_7H_6ClFS$; Calc.: % C, 47.6; % H, 3.42; % S, 18.2; Found: % C, 47.5; % H, 3.32; % S, 18.2; $^1$H NMR(CDCl$_3$): 7.12(m, 3H), 2.47(s, 3H).

2. Preparation of 4-Bromo-3-chloro-2-fluorothioanisole

A solution of 4.0 g (23 mmol) of 3-chloro-2-fluorothioanisole in 50 mL of dichloroethane was prepared and a catalytic amount (0.15 g, 1.2 mmol) of ferric chloride and 1.5 mL (30 mmol) of bromine were added. The mixture was heated to $40°$ C. with stirring for 2 hours. The solution was then cooled to ambient temperature and 20 mL of dilute aqueous sodium bisulfite was added. The mixture was stirred until the dichloromethane layer was colorless (15 min). The organic phase was recovered and the aqueous phase was extracted with more dichloromethane. The organic phase and extract were combined and dried over sodium sulfate. The volatiles were removed by evaporation under reduced pressure to obtain 5.0 g (85 percent of theory) of the title compound as a tan oil. $^1$H NMR(CDCl$_3$): 7.35(d, 1H, 7.2 Hz), 7.01(d, 1H, J=7.2 Hz), 2.44(s, 3H)

3. Preparation of 4-Bromo-3-chloro-2-fluoromethylsulfonylbenzene

Hydrogen peroxide (4.0 mL of 30 percent) was added with stirring to a solution of 5.0 g (20 mmol) of 4-bromo-3-chloro-2-fluorothioanisole in 50 mL of acetic acid. The mixture was heated at $50°$ C. for 3 hours and then cooled to ambient temperature. Most of the acetic acid was removed by evaporation under reduced pressure and the residue was diluted with water and extracted with dichloromethane. The extract was dried over sodium sulfate and concentrated by evaporation under reduced pressure to obtain 4.5 g (78 percent of theory) of the title compound as a white solid melting at $149°$ C.

Elemental Analysis $C_7H_5BrClFO_2S$; Calc.: % C, 29.2; % H, 1.75; % S, 11.1; Found: % C, 29.3; % H, 1.83; % S, 11.2; $^1$H NMR(CDCl$_3$): 7.7(m, 2H), 3.23(s, 3H).

4. Preparation of 2-Chloro-3-fluoro-4-methylsulfonylbenzoic Acid

A solution of 23 g (80 mmol) of 4-bromo-3-chloro-2-fluoromethylsulfonylbenzene in 100 mL of methanol was placed in a 300 mL stirred Parr bomb reactor and nitrogen was bubbled through the solution for 15 min. Triethylamine (28 mL, 200 mmol), palladium (II) acetate (0.90 g, 4.0 mmol), and 1,4-bis(diphenylphosphino)butane (3.4 g, 8.0 mmol) were then added and the bomb was sealed. The sealed bomb was charged with 300 psig (21,700 kiloPascals) of carbon monoxide and heated to $95°$ C. for 15 hours. The resulting solution was concentrated by evaporation under reduced pressure to remove the volatiles and the resulting slurry was diluted with 150 mL of 2N aqueous sodium hydroxide and stirred for 2 hr. The homogenous aqueous solution obtained was washed with dichloromethane and acidified with 2N aqueous hydrochloric acid. The resulting solution was extracted with ethyl acetate and the extract was dried over sodium sulfate and concentrated by evaporation under reduced pressure to obtain 10 g (63 percent of theory) of the title compound as a white solid melting at $204°$ C.

Elemental Analysis $C_8H_6ClFO_4S$; Calc.: % C, 38.0; % H, 2.39; % S, 12.7; Found: % C, 38.3; % H, 2.50; % S, 12.3; $^1$H NMR(CDCl$_3$): 3.43(s, 3H) 7.88(m, 2H).

5. Preparation of 2,3-Difluoro-4-methylthiobenzoic Acid

A 2.5M solution of butyllithium in hexane (4.5 mL, 11 mmol) was added dropwise with stirring to a solution of 1.00 mL (10.2 mmol) of 1,2-difluorobenzene in 10 mL of dry tetrahydrofuran cooled to $-70°$ C. under a nitrogen atmosphere. After 10 min, 0.80 mL (11 mmol) of dimethyl disulfide was added dropwise with stirring. Another 11 mmol of 2.5M butyllithium was then added and, after 10 min, the reaction mixture was quenched by bubbling a stream of dry carbon dioxide into the solution. The resulting mixture was diluted with water and the mixture was washed with ether and then acidified with 1N aqueous hydrochloric acid. The resulting heavy white precipitate was recrystallized from a mixture of ethyl acetate and heptane to obtain 0.65 g (31 percent of theory) of the title compound as a white solid melting at 214–215° C.

Elemental Analysis $C_8H_6F_2O_2S$; Calc.: % C, 47.1; % H, 2.96; Found: % C, 47.1; % H, 3.07; $^1$H NMR(DMSO-d$_6$): 7.65(m, 1H), 7.22(m, 1H), 2.57(s, 3H).

6. Preparation of 1-Ethyl-4-(2,3-dichloro-4-methylsulfonylbenzoyl)-5-hydroxypyrazole A solution of 500 mg (1.85 mmol) of 2,3-dichloro-4-methylsulfonylbenzoic acid and 240 mg (2.14 mmol) of 1-ethyl-5-hydroxypyrazole in 10 mL of dry acetonitrile was treated with 430 mg (2.08 mmol) of dicyclohexylcarbodiimide with stirring at ambient temperature for 0.5 hr. The precipitate that formed was removed by filtration and the filtrate was treated with 0.5 mL of triethylamine and 1 mL of acetone cyanohydrin. After 1 hr, the reaction mixture was partitioned between dichloromethane and 1N aqueous hydrochloric acid. The organic layer was recovered and extracted with dilute aqueous sodium bicarbonate solution. The basic aqueous solution obtained was acidified with dilute aqueous hydrochloric acid and extracted with dichloromethane. The organic extract was dried over sodium sulfate and concentrated by evaporation under reduced pressure to obtain 540 mg (81 percent of theory )of the title compound as an orange syrup.

$^1$H NMR(CDCl$_3$): 8.20(d, 1H, J=8.0 Hz), 7.52(d, 1H, J=8.0 Hz), 7.31(s, 1H), 4.05(q, 2H, J=7.3 Hz) 3.34(s, 3H), 1.45(t, 3H, J=7.3 Hz).

7. Preparation of 3-Hydroxyoxetane

Epichlorohydrin (92.5 g, 1.0 mol) was dissolved in 61.2 g (1.0 mol) of glacial acetic acid and 0.35 g of ferric chloride was added. The mixture was stirred at 65° C. overnight. Another 0.35 g of ferric chloride was added and the mixture was stirred another day. It was then concentrated by evaporation under reduced pressure to obtain 153 g 3-chloro-2-hydroxypropyl acetate as an oil. A few crystals of p-toluenesulfonic acid were added and then 81.5 g (1.13 mol) of ethyl vinyl ether was added dropwise with stirring and cooling with an ice bath to keep the temperature below about 35° C. When the addition was complete, the mixture was stirred overnight at 40° C. The dark oily product was presumed to be 3-chloro-2-(1-ethoxyethoxy)propyl acetate. This oil was added dropwise with stirring to a mixture of 110 g (2.75 mol) of sodium hydroxide in 110 mL of water heated to 105° C. When the addition was complete, the mixture was heated at 105° C. with stirring for 4 hours. It was then cooled and poured into 500 mL of water. The resulting mixture was extracted with 2×500 mL of diethyl ether and the ethereal extract was washed with concentrated aqueous sodium chloride, dried over sodium sulfate, and concentrated by evaporation under reduced pressure at 30° C. to obtain a dark oil. This oil was distilled at 5 mm Hg (665 pascals) pressure. The 40 g portion boiling at 60–68° C., which was 3-(1-ethoxyethoxy)oxetane, was collected. This fraction was dissolved in 100 mL of methanol and 25 mg of p-toluenesulfonic acid was added with stirring at about 10° C. The mixture was stirred for 2 hours at ambient temperature and then 1.0 g of solid sodium bicarbonate was added with stirring. After 5 min, the mixture was filtered and concentrated by evaporation under reduce pressure. The colorless oil residue was distilled at 5 mm Hg (665 pascals) pressure and the 1.9 g fraction boiling at 50–56° C., which was the title compound, a colorless liquid, was collected.

8. Preparation of 2-Chloro-4-methylsulfonyl-3-(3-oxetanyloxy)benzoic acid

A mixture of 0.76 g (19 mmol) of 60 percent in mineral oil sodium hydride in dry N,N-dimethylformamide was prepared in a flask under a nitrogen blanket and to it was added 2.02 g (8.0 mmol) of 2-chloro-3-fluoro-4-methylsulfonylbenzoic acid in portions with stirring at ambient temperature. The mixture was allowed to cool and then 0.71 g (9.6 mmol) of 3-hydroxyoxetane was added dropwise with stirring. There was an exotherm. After one hour, the reaction appeared to be complete and water was added cautiously. The resulting aqueous solution was extracted with ether and was then acidified with 1N aqueous hydrochloric acid. The resulting mixture was extracted three times with ethyl acetate and the three extracts were combined, washed with water, dried over magnesium sulfate, and concentrated by evaporation under reduced pressure. The residue was crystallized with a mixture of acetone and hexane to obtain 1.41 g of the title compound as white crystals melting at 180–183° C.

Elemental Analysis $C_{11}H_{11}ClO_6S$; Calc.: % C, 43.1; % H, 3.61; % S, 10.5; Found: % C, 43.0; % H, 3.75; % S, 10.4;

9. Preparation of 1-Ethyl-4-(2-chloro-4-methylsulfonyl-3-(3-oxetanyloxy)benzoyl)-5-hydroxypyrazole (Compound 1)

Dicyclohexylcarbodiimide (0.72 g (3.5 mmol) was added at ambient temperature with stirring to a solution of 1.07 g (3.5 mmol) of 2-chloro-4-methylsulfonyl-3-(3-oxetanyloxy) benzoic acid and 0.45 g (4 mmol) of 1-ethyl-5-hydroxypyrazole in 25 mL of dry acetonitrile. The mixture was allowed to react for about one hour and then was filtered. The solids collected were extracted with dry acetonitrile. The filtrate and extract were combined and 0.69 g (5.0 mmol) of potassium carbonate and a few drops of acetone cyanohydrin were added with stirring at ambient temperature. The mixture was stirred overnight and was then poured into water. The resulting solution was extracted with ether and then acidified with aqueous hydrochloric acid. The mixture obtained was extracted three times with dichloromethane and the three extracts were combined, washed with water, dried over magnesium sulfate, and concentrated by evaporation under reduced pressure. The yellow solid residue was recrystallized from ethanol to obtain 0.77 g (55 percent of theory) of the title compound as a nearly colorless solid melting at 206–2080° C.

Elemental Analysis $C_{16}H_{17}ClN_2O_6S$; Calc.: % C, 47.9; % H, 4.27; % N, 6.99; % S, 8.00; Found: % C, 47.7; % H, 4.18; % N, 6.86; % S, 8.04;

10. Preparation of 1-Methyl-4-(2-chloro-4-methyl-sulfonyl-3-(3-oxetanyloxy)benzoyl)-5-hydroxypyrazole (Compound 2)

Sodium hydride as a 60% mixture in mineral oil (0.32 g (8 mmol)) was added in portions with stirring to a solution of 1.0 g (2 mmol) of 1-methyl-4-(2,3-dichloro-4-methylsulfonylbenzoyl)-5-hydroxypyrazole and 0.30 g (4 mmol) of 3-hydroxyoxetane in N,N-dimethylformamide. The mixture was stirred overnight and then 25 mL of water were added. The resulting mixture was extracted with 50 mL of diethyl ether and then acidified with 2N aqueous hydrochloric acid. The resulting mixture was extracted with dichloromethane. The organic extract was washed with saturated aqueous sodium chloride, dried over sodium sulfate, and concentrated by evaporation under reduced pressure. The reddish oil residue was purified by reverse phase preparative chromatography, eluting with a 40:60 acetonitrile mixture with water. The first major peak was recovered by extracting with dichloromethane, drying the extract over sodium sulfate, and concentrating by evaporation under reduced pressure. The resulting solids were recrystallized from ethanol to obtain 0.41 g of the title compound, a white solid melting at 225–227° C.

Elemental Analysis $C_{15}H_{15}ClN_2O_6S$; Calc.: % C, 46.6; % H, 3.91; % N, 7.24; Found: % C, 46.6; % H, 3.94; % N, 7.20.

The following compounds were prepared similarly:

1-Methyl-4-(2-methyl-4-methylsulfonyl-3-(3-oxetanyloxy)-benzoyl)-5-hydroxypyrazole (Compound 3), a white solid melting at 200–202° C. (from 1-methyl-4-(3-fluoro-2-methyl-4-methylsulfonylbenzoyl)-5-hydroxypyrazole).

Elemental Analysis $C_{16}H_{18}N_2O_6S$; Calc.: % C, 52.5; % H, 4.95; % N, 7.65; Found: % C, 52.4; % H, 4.91; % N, 7.57.

1-Ethyl-4-(2-methyl-4-methylsulfonyl-3-(3-oxetanyloxy)-benzoyl)-5-hydroxypyrazole (Compound 4), a white solid melting at 185–187° C. (from 1-ethyl-4-(3-fluoro-2-methyl-4-methylsulfonylbenzoyl)-5-hydroxypyrazole).

Elemental Analysis $C_{17}H_{20}N_2O_6S$; Calc.: % C, 53.7; % H, 5.30; % N, 7.36; Found: % C, 53.6; % H, 5.26; % N, 7.31.

1-Ethyl-4-(2-chloro-4-methylsulfonyl-3-(2-(2-oxetanyl)ethoxy)benzoyl)-5-hydroxypyrazole (Compound 5), melting at 142–144° C. Elemental Analysis $C_{18}H_{21}ClN_2O_6S$; Calc.: % C, 50.41; % H, 4.94; % N, 6.53; Found: % C, 50.52; % H, 5.00; % N, 6.45.

1-Ethyl-3-methyl-4-(2-chloro-4-methylsulfonyl-3-(3-oxetanyloxy)benzoyl)-5-hydroxypyrazole (Compound 6), a foam. Mass spectrum M$^+$ 414.

1,3-Dimethyl-4-(2-chloro-4-methylsulfonyl-3-(3-oxetanyloxy)benzoyl)-5-hydroxypyrazole (Compound 7), a foam. Elemental Analysis $C_{16}H_{17}ClN_2O_6S$; Calc.: % C, 47.94; % H, 4.27; % N, 6.99; Found: % C, 47.87; % H, 4.33; % N, 6.98.

1-Ethyl-4-(2-chloro-4-methylsulfonyl-3-((3-methyl-3-oxetanyl)methoxy)benzoyl)-5-hydroxypyrazole (Compound 8), melting at 197–199° C. Elemental Analysis $C_{18}H_{21}ClN_2O_6S$; Calc.: % C, 50.41; % H, 4.94; % N, 6.53; Found: % C, 50.32; % H, 4.95; % N, 6.45.

1-Ethyl-4-(2-methyl-4-methylsulfonyl-3-((3-methyl-3-oxetanyl)methoxy)benzoyl)-5-hydroxypyrazole (Compound 9), melting at 147–150° C. Elemental Analysis $C_{19}H_{24}N_2O_6S$; Calc.: % C, 55.87; % H, 5.92; % N, 6.86; Found: % C, 55.54; % H, 5.91; % N, 6.61.

1-Ethyl-4-(2-chloro-4-methylsulfonyl-3-(2-oxetanylmethoxy)benzoyl)-5-hydroxypyrazole (Compound 10), melting at 153–156° C. Elemental Analysis $C_{17}H_{19}ClN_2O_6S$; Calc.: % C, 49.22; % H, 4.62; % N, 6.75; Found: % C, 49.04; % H, 4.68; % N, 6.61.

1-Methyl-4-(2-chloro-4-methylsulfonyl-3-(2-oxetanylmethoxy)benzoyl)-5-hydroxypyrazole (Compound 11), melting at 176–179° C. Elemental Analysis $C_{16}H_{17}ClN_2O_6S$; Calc.: % C, 47.94; % H, 4.27; % N, 6.99; Found: % C, 47.60; % H, 4.28; % N, 7.00.

1,3-Dimethyl-4-(2-chloro-4-methylsulfonyl-3-(2-oxetanylmethoxy)benzoyl)-5-hydroxypyrazole (Compound 12), a foam. Mass spectrum M$^+$ 414.

1-Ethyl-3-methyl-4-(2-chloro-4-methylsulfonyl-3-(2-oxetanylmethoxy)benzoyl)-5-hydroxypyrazole (Compound 13), a foam. Elemental Analysis $C_{18}H_{21}ClN_2O_6S$; Calc.: % C, 50.41; % H, 4.94; % N, 6.53; Found: % C, 49.68; % H, 4.96; % N, 6.16.

1-Ethyl-4-(2-methyl-4-methylsulfonyl-3-(2-oxetanylmethoxy)benzoyl)-5-hydroxypyrazole (Compound 14), melting at 141–144° C. Elemental Analysis $C_{18}H_{22}ClN_2O_6S$; Calc.: % C, 54.81; % H, 5.62; % N, 7.10; Found: % C, 54.84; % H, 5.61; % N, 7.16.

1-Methyl-4-(2-methyl-4-methylsulfonyl-3-(2-oxetanylmethoxy)benzoyl)-5-hydroxypyrazole (Compound 15), melting at 179–181° C. Elemental Analysis $C_{17}H_{20}N_2O_6S$; Calc.: % C, 53.67; % H, 5.30; % N, 7.36; Found: % C, 53.59; % H, 5.29; % N, 7.26.

11. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximately 15 hr photo-period which was maintained at about 23–29° C. during the day and 22–28° C. during the night. Nutrients and water were added on a regular basis and supplemental lighting was provided with overhead metal halide 1000 Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The concentrated stock solutions obtained were diluted with an aqueous mixture containing acetone, water, isopropyl alcohol, dimethyl sulfoxide, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by serial dilution of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kilopascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 1.

TABLE 1

POSTMERGENCE HERBICIDAL ACTIVITY

| Cpd. No. | Rate, ppm | BWCHK | BWCKB | BWLMQ | BWPIG | BWVEL | BWVIO | BWWBK | GWBLG | GWBRN | GWCRB | GWGFT | GWROX | GWWOT |
|---|---|---|---|---|---|---|---|---|---|---|---|---|---|---|
| 1 | 15.6 | 90 | 90 | 98 | 100 | 98 | 60 | 100 | 90 | 100 | 95 | 98 | 100 | 95 |
| 2 | 15.6 | 90 | 90 | 98 | 100 | 85 | 80 | 95 | 50 | 98 | 95 | 98 | 98 | 85 |
| 3 | 7.8 | 95 | 90 | 98 | 100 | 95 | 30 | 80 | 80 | 100 | 95 | 95 | 100 | 90 |
| 4 | 7.8 | 95 | 90 | 98 | 100 | 90 | 60 | 98 | 90 | 100 | 98 | 98 | 100 | 95 |
| 5 | 125 | 85 | 90 | 95 | 30 | 70 | 40 | 85 | 10 | 85 | 85 | 85 | 95 | 20 |
| 6 | 125 | 95 | 90 | 100 | 100 | 75 | 60 | 85 | 70 | 100 | 100 | 95 | 95 | 70 |
| 7 | 125 | 80 | 90 | 98 | 100 | 70 | 60 | 70 | 30 | 100 | 95 | 90 | 90 | 85 |
| 8 | 125 | 60 | 90 | 100 | 100 | 90 | 85 | 75 | 70 | 100 | 95 | 95 | 100 | 98 |
| 9 | 125 | 100 | 90 | 100 | 100 | 85 | 95 | 98 | 95 | 95 | 95 | 98 | 95 | 100 |
| 10 | 125 | 100 | 95 | 100 | 100 | 100 | 98 | 98 | 40 | 95 | 98 | 95 | 100 | 100 |
| 11 | 125 | 90 | 95 | 90 | 100 | 98 | 80 | 98 | 30 | 95 | 95 | 98 | 98 | 50 |
| 12 | 125 | 85 | 80 | 90 | 95 | 75 | 80 | 70 | 30 | 90 | 90 | 95 | 70 | 80 |
| 13 | 125 | 70 | 85 | 90 | 90 | 70 | 75 | 70 | 50 | 95 | 80 | 85 | 70 | 50 |
| 14 | 125 | 98 | 95 | 100 | 100 | 98 | 70 | 100 | 70 | 100 | 98 | 98 | 100 | 100 |
| 15 | 125 | 100 | 100 | 95 | 95 | 95 | 60 | 95 | 30 | 95 | 95 | 95 | 98 | 95 |

BWCHK = chickweed (*Stellaria media*)
BWCKB = cocklebur (*Xanthium strumarium*)
BWLMQ = lambsquarters (*Chenopodium album*)
BWPIG = pigweed (*Amaranthus retroflexus*)
BWVEL = velvetleaf (*Abutilon theophrasti*)
BWVIO = viola (*Viola tricolor*)
BWWBK = wild buckwheat (*Polygonum convolvulus*)
GWBLG = blackgrass (*Alopecurus myosuroides*)
GWBRN = barnyardgrass (*Echinochloa crus-galli*)
GWCRB = crabgrass (*Digitaria sanguinalis*)
GWGFT = giant foxtail (*Setaria faberi*)
GWROX = Rox orange sorghum (*Sorghum bicolor*)
GWWOT = wild oats (*Avena fatua*)

12. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 113 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 2 mL aliquots of the stock solution with 15 mL of the mixture and lower concentrations were prepared by serial dilution of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture.

A highest application rate of 4.48 Kg/Ha is achieved when 68.8 mg of test compound is employed.

The treated pots and control pots were placed in a greenhouse with an approximately 15 hr photoperiod which was maintained at about 23–29° C. during the day and 22–28° C. during the night. Nutrients and water were added on a regular basis and supplemental lighting was provided with overhead metal halide 1000 Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are given in Table 2.

TABLE 2

PREEMERGENCE HERBICIDAL ACTIVITY

| Cpd. No. | Rate, g/Ha | BWCKB | BWLMQ | BWPIG | BWVEL | BWWPT | GWBLG | GWBRN | GWCRB | GWGFT | GWROX | GWWOT |
|---|---|---|---|---|---|---|---|---|---|---|---|---|
| 1 | 17.5 | 100 | 100 | 100 | 100 | 60 | 0 | 99 | 100 | 75 | 60 | 10 |
| 2 | 35 | 10 | 100 | 100 | 100 | 0 | 0 | 70 | 100 | 60 | 10 | 40 |
| 3 | 35 | 20 | 100 | 100 | 100 | 40 | 5 | 100 | 100 | 100 | 40 | 70 |
| 4 | 17.5 | 20 | 100 | 100 | 100 | 20 | 30 | 99 | 100 | 100 | 10 | 50 |
| 5 | 140 | 100 | 100 | 98 | 100 | 40 | 100 | 100 | 100 | 100 | 80 | 50 |
| 6 | 140 | 100 | 100 | 100 | 100 | 70 | 0 | 100 | 100 | 100 | 100 | 80 |
| 7 | 140 | 100 | 100 | 100 | 100 | 98 | 100 | 100 | 100 | 100 | 100 | 90 |
| 8 | 140 | 80 | 100 | 100 | 100 | 20 | 0 | 100 | 100 | 100 | 100 | 85 |
| 9 | 140 | 100 | 100 | 100 | 100 | 100 | 100 | 100 | 100 | 100 | 100 | 70 |
| 10 | 140 | 100 | 100 | 100 | 100 | 60 | 60 | 100 | 100 | 100 | 100 | 50 |
| 11 | 140 | 85 | 100 | 100 | 100 | 100 | 0 | 100 | 100 | 100 | 100 | 0 |
| 12 | 140 | 90 | 100 | 100 | 100 | 80 | 30 | 100 | 100 | 100 | 100 | 100 |
| 13 | 140 | 100 | 100 | 100 | 100 | 100 | 20 | 100 | 100 | 100 | 98 | 100 |
| 14 | 140 | 100 | 100 | 100 | 100 | 90 | 20 | 100 | 100 | 100 | 100 | 100 |
| 15 | 140 | 85 | 100 | 100 | 100 | 100 | 20 | 100 | 100 | 100 | 100 | 70 |

BWCKB = cocklebur (*Xanthium strumarium*)
BWLMQ = lambsquarters (*Chenopodium album*)
BWMGL = morningglory (*Ipoinoea hederacea*)
BWPIG = pigweed (*Amaranthus retroflexus*)
BWVEL = velvetleaf (*Abutilion theophrasti*)
BWWPT = wild poinsettia (*Euphorbia heterophylla*)
GWBLG = blackgrass (*Alopecurus myosuroides*)
GWBRN = barnyardgrass (*Echinochloa crusgalli*)
GBCRB = crabgrass (*Digitaria sanguinalis*)
GWGFT = giant foxtail (*Setaria faberi*)
GWRQX = Rox orange sorghum (*Sorghum bicolor*)
GWWOT = wild oats (*Avena fatua*)

What is claimed is:

1. A benzoylpyrazole compound of the formula:

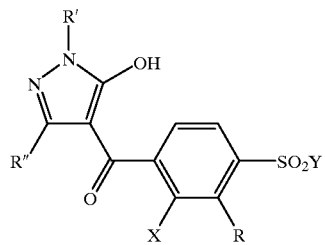

wherein

X represents F, Cl, Br, $CH_3$ or $OCH_3$;

Y represents $CH_3$, $C_2H_5$, or $CH(CH_3)_2$;

R represents 3-oxetanyloxy, 3-oxetanylmethoxy, or 2-oxetanylmethoxy, each optionally substituted with methyl;

R' represents $C_1$–$C_4$ alkyl, $C_3$–$C_4$ alkenyl, or $C_3$–$C_4$ alkynyl;

R" represents H or $CH_3$;

and the agriculturally acceptable salts and esters thereof.

2. A compound according to claim 1 wherein Y represents methyl.

3. A compound according to claim 1 wherein X represents chloro or methyl.

4. A compound according to claim 1 wherein R" represents hydrogen.

5. A compound according to claim 1 wherein R' represents methyl or ethyl.

6. A compound according to claim 1 wherein R represents a 3-oxetanyloxy moiety:

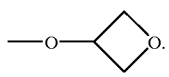

7. A compound according to claim 6 which is 1-ethyl-4-(2-methyl-3-(3-oxetanyloxy)-4-methylsulfonylbenzoyl)-5-hydroxypyrazole or an agriculturally acceptable salt or ester thereof.

8. A compound according to claim 6 which is 1-ethyl-4-(2-chloro-3-(3-oxetanyloxy)-4-methylsulfonylbenzoyl)-5-hydroxypyrazole or an agriculturally acceptable salt or ester thereof.

9. A herbicidal composition comprising an herbicidally effective amount of a benzoylpyrazole compound of the formula:

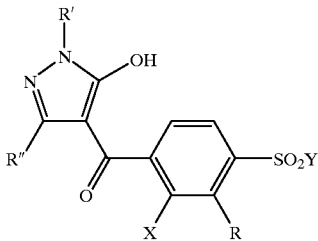

wherein

X represents F, Cl, Br, $CH_3$ or $OCH_3$;

Y represents $CH_3$, $C_2H_5$, or $CH(CH_3)_2$;

R represents 3-oxetanyloxy, 3-oxetanylmethoxy, or 2-oxetanylmethoxy, each optionally substituted with methyl;

R' represents $C_1$–$C_4$ alkyl, $C_3$–$C_4$ alkenyl, or $C_3$–$C_4$ alkynyl;

R" represents H or $CH_3$;

or an agriculturally acceptable salt or ester thereof in admixture with an agriculturally acceptable adjuvant or carrier.

10. A composition according to claim 9 wherein Y represents methyl.

11. A composition according to claim 9 wherein X represents chloro or methyl.

12. A composition according to claim 9 wherein R" represents hydrogen.

13. A composition according to claim 9 wherein R' represents methyl or ethyl.

14. A composition according to claim 9 wherein R represents a 3-oxetanyloxy moiety:

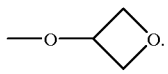

15. A composition according to claim 14 wherein the benzoylpyrazole compound is 1-ethyl-4-(2-methyl-3-(3-oxetanyloxy)-4-methylsulfonylbenzoyl)-5-hydroxypyrazole or an agriculturally acceptable salt or ester thereof.

16. A composition according to claim 14 wherein the benzoylpyrazole compound is 1-ethyl-4-(2-chloro-3-(3-oxetanyloxy)-4-methylsulfonylbenzoyl)-5-hydroxypyrazole or an agriculturally acceptable salt or ester thereof.

17. A method of controlling undesirable vegetation which comprises contacting the vegetation or the locus thereof with an herbicidally effective amount of a benzoylpyrazole compound of the formula:

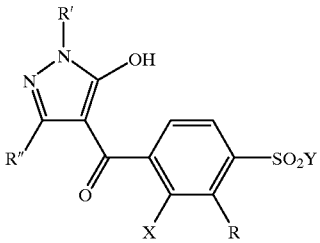

wherein

X represents F, Cl, Br, $CH_3$ or $OCH_3$;

Y represents $CH_3$, $C_2H_5$, or $CH(CH_3)_2$;

R represents 3-oxetanyloxy, 3-oxetanylmethoxy, or 2-oxetanylmethoxy, each optionally substituted with methyl;

R' represents $C_1$–$C_4$ alkyl, $C_3$–$C_4$ alkenyl, or $C_3$–$C_4$ alkynyl;

R" represents H or $CH_3$;

or an agriculturally acceptable salt or ester thereof.

18. A method according to claim 17 wherein Y represents methyl.

19. A method according to claim 17 wherein X represents chloro or methyl.

20. A method according to claim 17 wherein R" represents hydrogen.

21. A method according to claim 17 wherein R' represents methyl or ethyl.

22. A method according to claim 17 wherein R represents a 3-oxetanyloxy moiety:

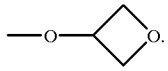

23. A method according to claim 22 wherein the benzoylpyrazole compound is 1-ethyl-4-(2-methyl-3-(3-oxetanyloxy)-4-methylsulfonylbenzoyl)-5-hydroxypyrazole or an agriculturally acceptable salt or ester thereof.

24. A method according to claim 22 wherein the benzoylpyrazole compound is 1-ethyl-4-(2-chloro-3-(3-oxetanyloxy)-4-methylsulfonylbenzoyl)-5-hydroxypyrazole or an agriculturally acceptable salt or ester thereof.

25. A method according to claim 17 wherein the undesirable vegetation is contacted postemergently.

26. A method according to claim 17 wherein the undesirable vegetation is contacted in the presence of a corn, wheat, barley, or rice crop.

27. A benzoic acid compound of the formula:

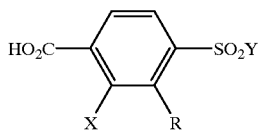

wherein

X represents F, Cl, Br, CH₃ or OCH₃;

Y represents CH₃, C₂H₅, or CH(CH₃)₂; and

R represents 3-oxetanyloxy, 3-oxetanylmethoxy, or 2-oxetanylmethoxy, each optionally substituted with methyl.

28. A compound according to claim 27 wherein Y represents methyl.

29. A compound according to claim 27 wherein X represents chloro or methyl.

30. A compound according to claim 27 wherein R represents a 3-oxetanyloxy moiety:

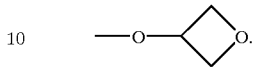

31. A compound according to claim 30 which is 2-methyl-3-(3-oxetanyloxy)-4-methylsulfonylbenzoic acid.

32. A compound according to claim 30 which is 2-chloro-3-(3-oxetanyloxy)-4-methylsulfonylbenzoic acid.

* * * * *